United States Patent [19]
Stoffel

[11] Patent Number: 5,168,766
[45] Date of Patent: Dec. 8, 1992

[54] AUTOMAT FOR ANALYZING BLOOD GROUPING WITH SPECIFICALLY FORMED SAMPLE SUPPORT

[75] Inventor: Francois Stoffel, Six-Fours, France

[73] Assignee: Gespac Instruments, La Seyne sur Mer, France

[21] Appl. No.: 660,939

[22] Filed: Feb. 26, 1991

[30] Foreign Application Priority Data
Mar. 2, 1990 [FR] France ................................ 90 02896

[51] Int. Cl.$^5$ ............................................. G01N 35/00
[52] U.S. Cl. ................................ 73/864.81; 436/45
[58] Field of Search ........... 73/864.81, 863.23, 863.24, 73/863.25; 436/45; 494/16, 31

[56] References Cited

U.S. PATENT DOCUMENTS

| | | | |
|---|---|---|---|
| 4,413,060 | 11/1983 | Assmann et al. | 436/45 |
| 4,883,763 | 11/1989 | Holen et al. | 436/45 |
| 4,927,545 | 5/1990 | Roginski | 436/45 |
| 4,961,915 | 10/1990 | Martin | 436/45 |
| 5,005,981 | 4/1991 | Schulte et al. | 494/16 |
| 5,061,446 | 10/1991 | Guigan | 436/45 |

Primary Examiner—Hezron E. Williams
Assistant Examiner—Howard Wisnia
Attorney, Agent, or Firm—Dowell & Dowell

[57] ABSTRACT

An automat for analyzing blood grouping, which includes a centrifuge for positioning and centrifuging micro-boards opposite supports articulated on the ends of a beam driven in rotation by a stepping motor, and a transfer clamp controlled along the x-axis XX' and y-axis YY' by two stepping motors so as to transport the micro-boards from the centrifuge to different work stations.

4 Claims, 7 Drawing Sheets

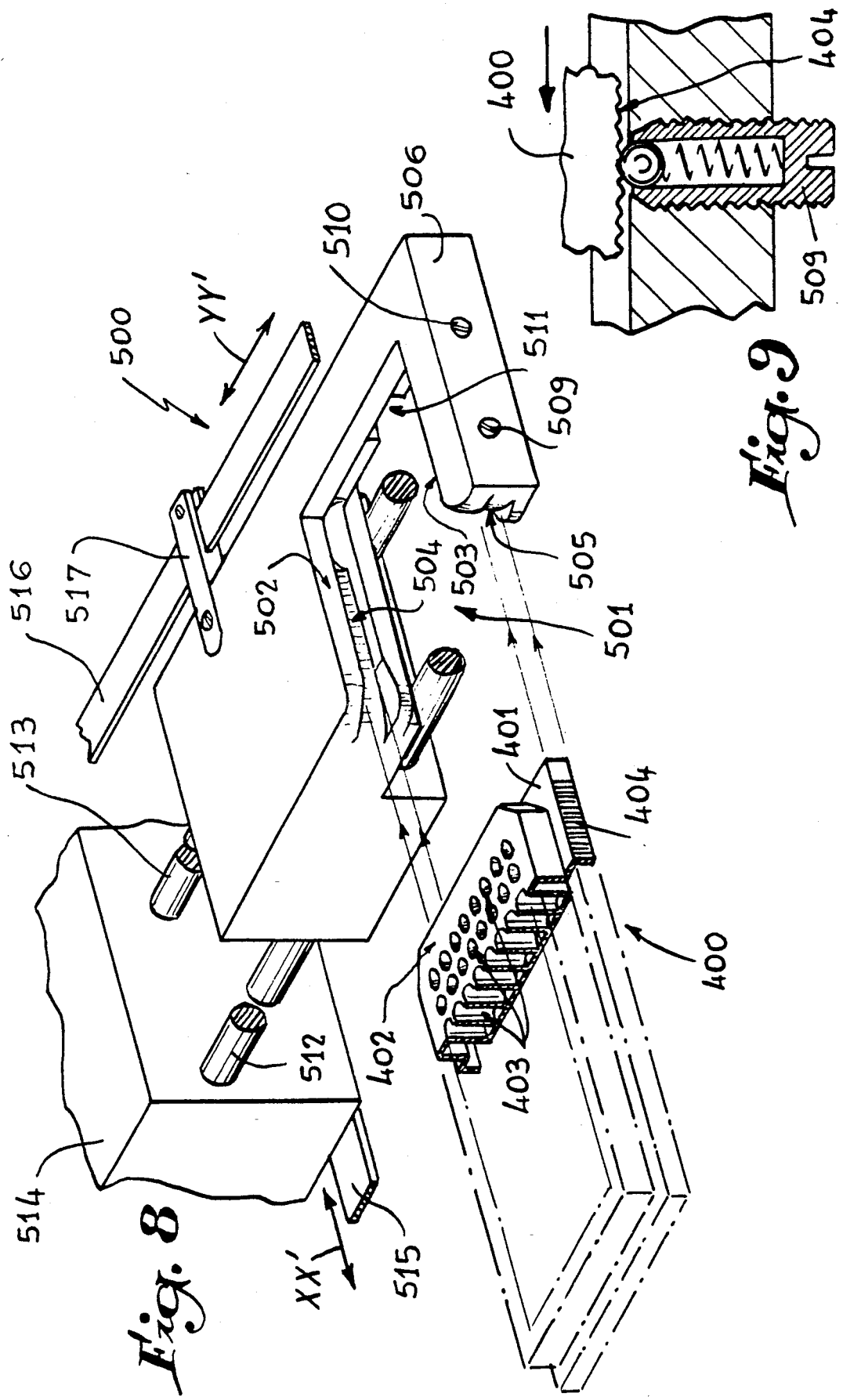

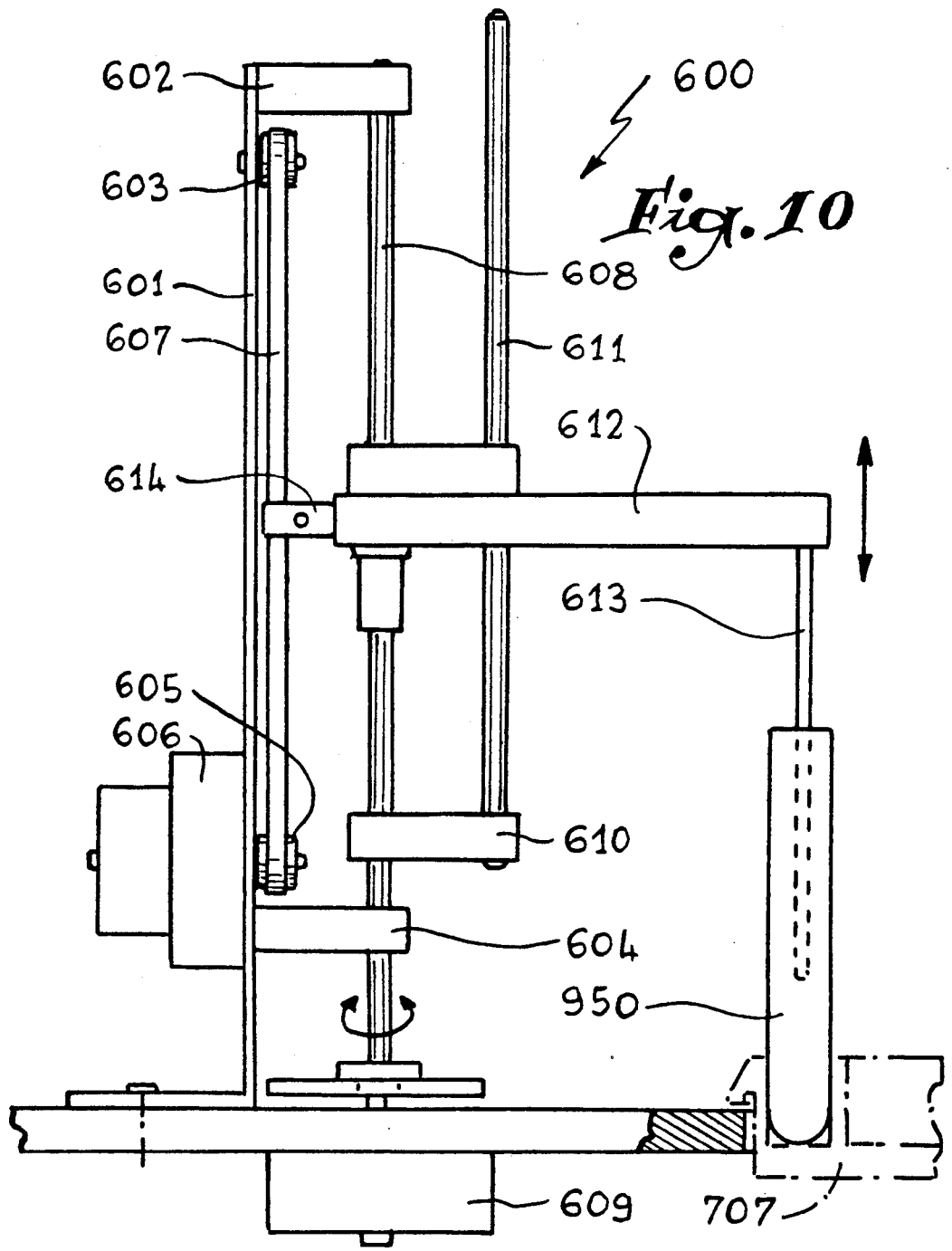

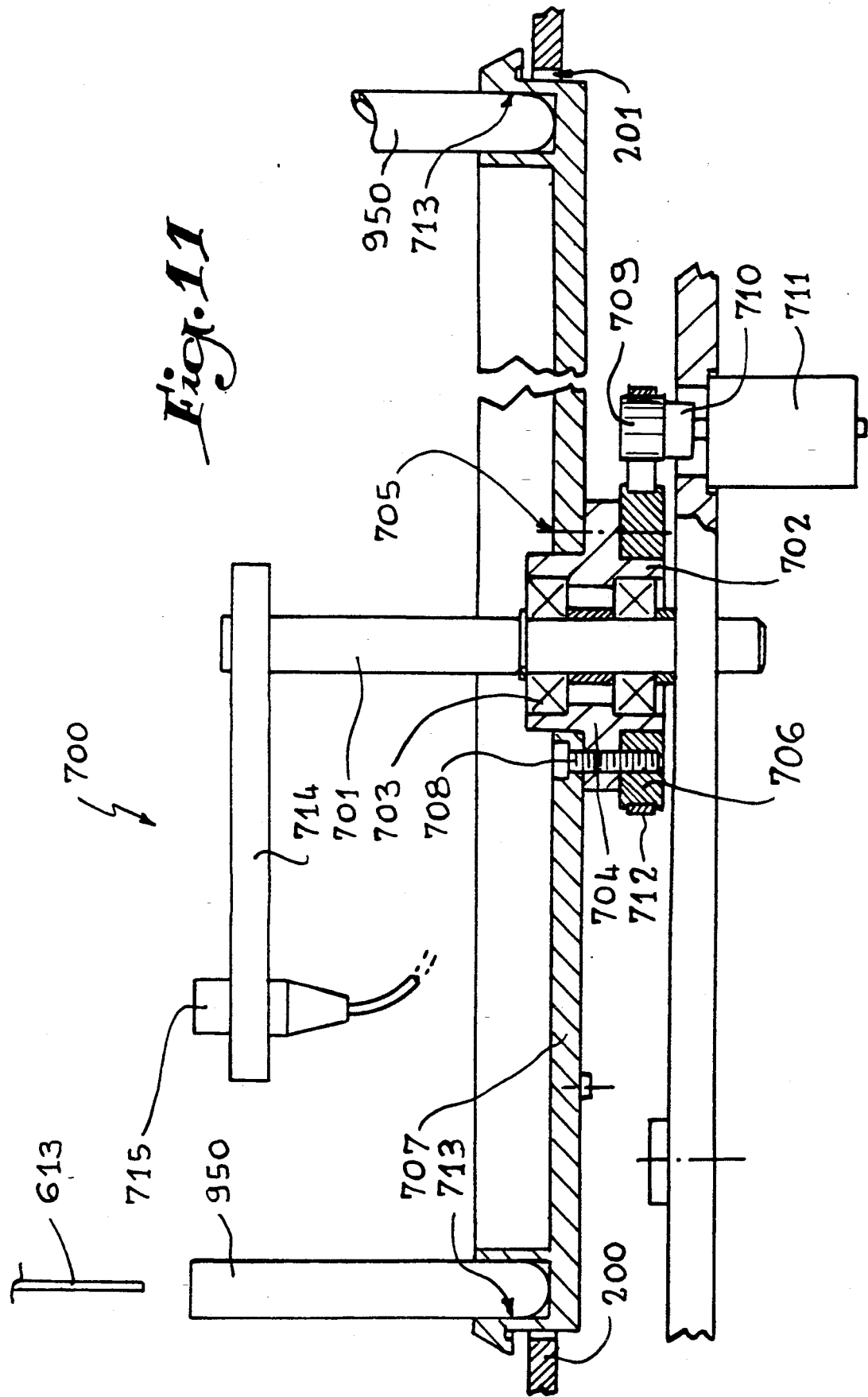

AUTOMAT FOR ANALYZING BLOOD GROUPING WITH SPECIFICALLY FORMED SAMPLE SUPPORT

BACKGROUND OF THE INVENTION

1. FIELD OF THE INVENTION

The present invention relates to the determination of blood groups.

2. History of the Related Art

In this domain, semi-automatic apparatus for dispensing the products to be mixed, are known. They generally comprise a test-tube changer provided on its periphery with a certain number of notches and associated with a sampling probe for transferring the products contained in the test-tubes. In the notches are disposed the test-tubes containing either centrifuged blood from each of the patients whose group is to be determined, or reagents of different contents and of which the number may vary depending on the type of analyses effected. The probe firstly samples a quantity of centrifuged blood of a patient and distributes it along a line or column of cells in a micro-board, and this for each patient; then it dispenses a reagent according to the same process, and this for each reagent so as to obtain the result of the type of analyses sought.

When dispensing of the different blood samples and reagents is terminated, the micro-board is transported by hand into a centrifuge so as to induce the reaction.

The micro-board is then placed by hand on a micro-board reader in order to analyze the results and determine the blood group of each of the patients. For the search to be considered as valid, it must be recommenced a second time, but with different reagents so as to confirm the first analysis.

It will be readily understood that such a analyzer procedure is tedious and complicated when the number of patients is high, this possibly leading to an error in reading which may have grave consequences.

It is an object of the present invention to overcome these drawbacks, more particularly by limiting the human interventions in order to reduce the risks of errors.

SUMMARY OF THE INVENTION

The present invention relates to an automat for analyzing blood grouping, characterized in that it comprises a centrifuge for positioning and centrifuging the micro-boards which includes two opposite supports, articulated on the ends of a beam driven in rotation by a D.C. motor, and a transfer clamp controlled along the x-axis XX' and y-axis YY' by two stepping motors so as to transport the micro-boards from the centrifuge to the different work stations set up on a table.

BRIEF DESCRIPTION OF THE DRAWINGS

The invention will be more readily understood on reading the following description with reference to the accompanying drawings, in which:

FIG. 8 is a view in perspective showing the clamping element for transporting the micro-boards.

FIG. 9 is a section showing the means for blocking the micro-board in the clamp.

FIG. 10 is a view of the station for sampling the products.

FIG. 11 is a view of the station for dispensing the products to be sampled.

DETAILED DESCRIPTION OF THE DRAWINGS

Figure 1:
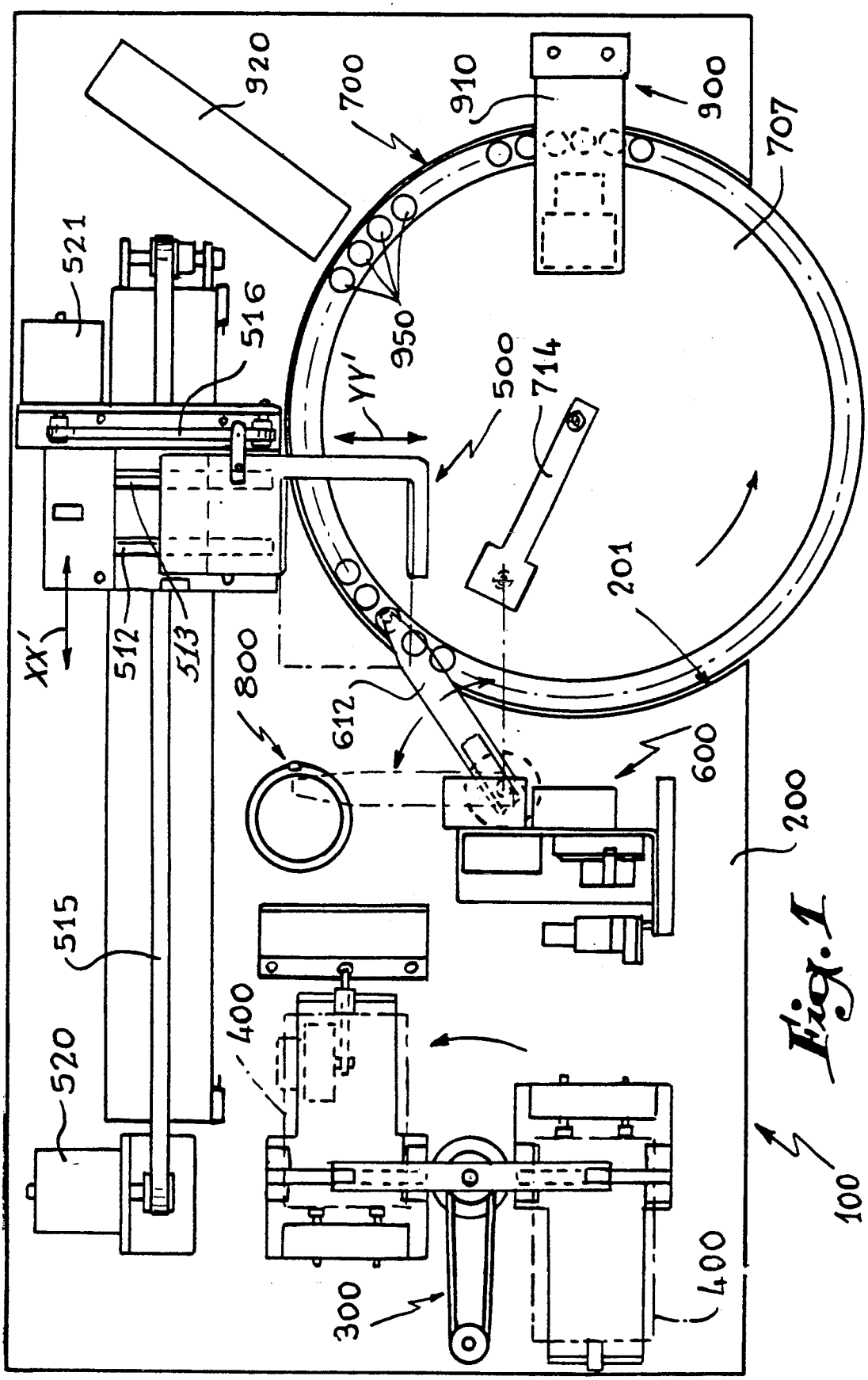
FIG. 1 is an overall view of the elements constituting the analyzer automat according to the invention.

Referring now to the drawings, FIG. 1 shows an analyzer automat 100 comprising a transfer table 200 on which different work stations are set up:

a station 300 for positioning and centrifuging micro-boards 400 shown in dashed and dotted lines;

a station 500 for transferring the micro-boards 400;

a station 600 for sampling the products to be distributed;

a station 700 for dispensing the products to be sampled;

a station 800 for reading the results of the reaction;

a station 900 for identifying the test-tubes 950.

Figure 2:
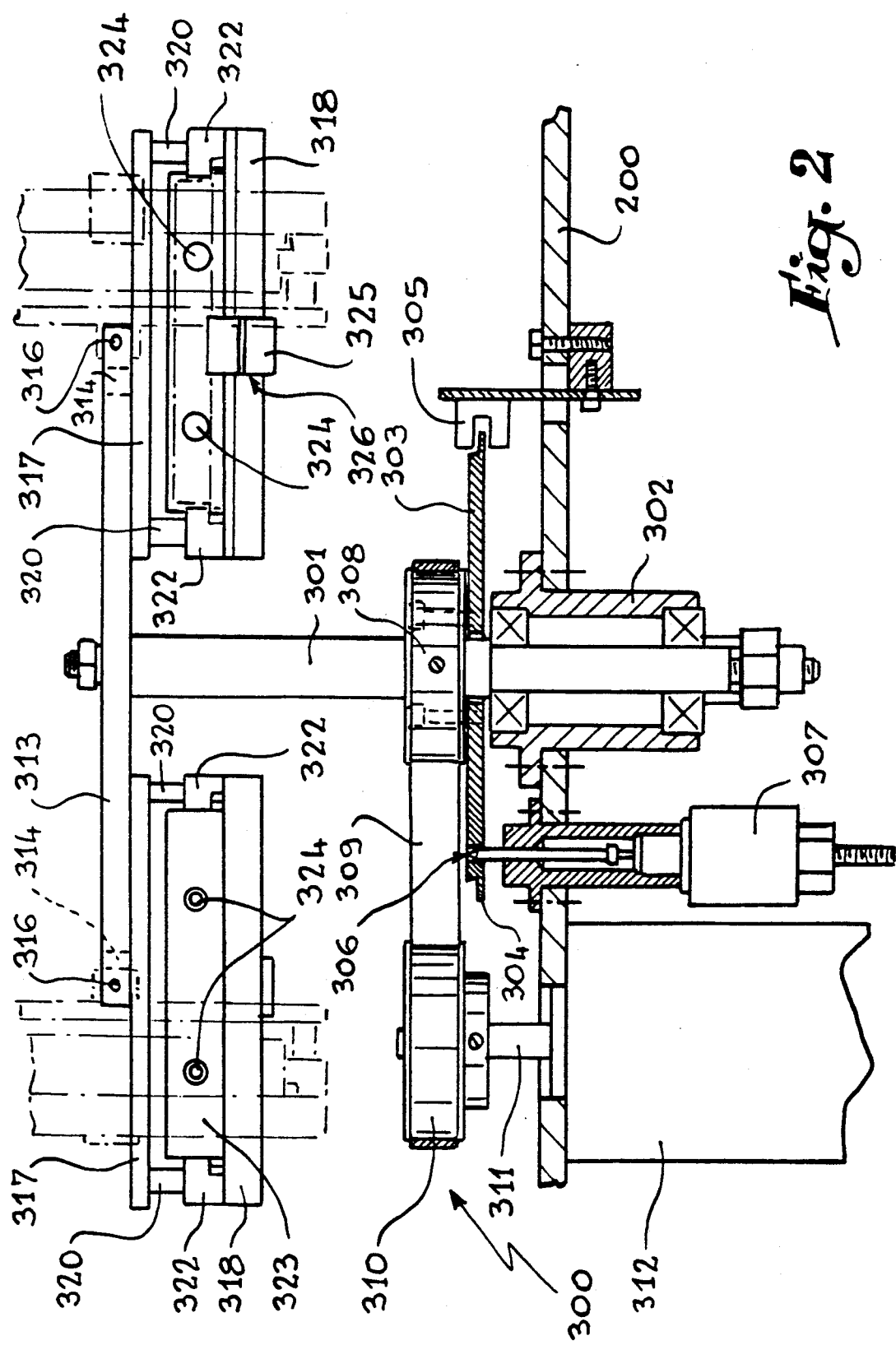
FIG. 2 is a section showing the station for centrifuging the micro-boards.

FIG. 2 illustrates the centrifugation station 300 which comprises a rotating shaft 301 guided axially by a roller bearing device 302 traversing vertically through the transfer table 200. Above the roller bearing device 302 is fixed a disc 303 handing on its periphery, a shoulder 304 which cooperates with a sensor 305, and an opening 306 which allows passage of an indexing finger 307 adapted to block the shaft 301 in one single position.

In the middle of the rotating shaft 301 is secured to a pulley 308 which, via a belt 309, is connected to another pulley 310 mounted at the free end of the driven shaft 311 of a D.C. motor 312 with a view to driving the shaft 301 in rotation.

Figure 3:
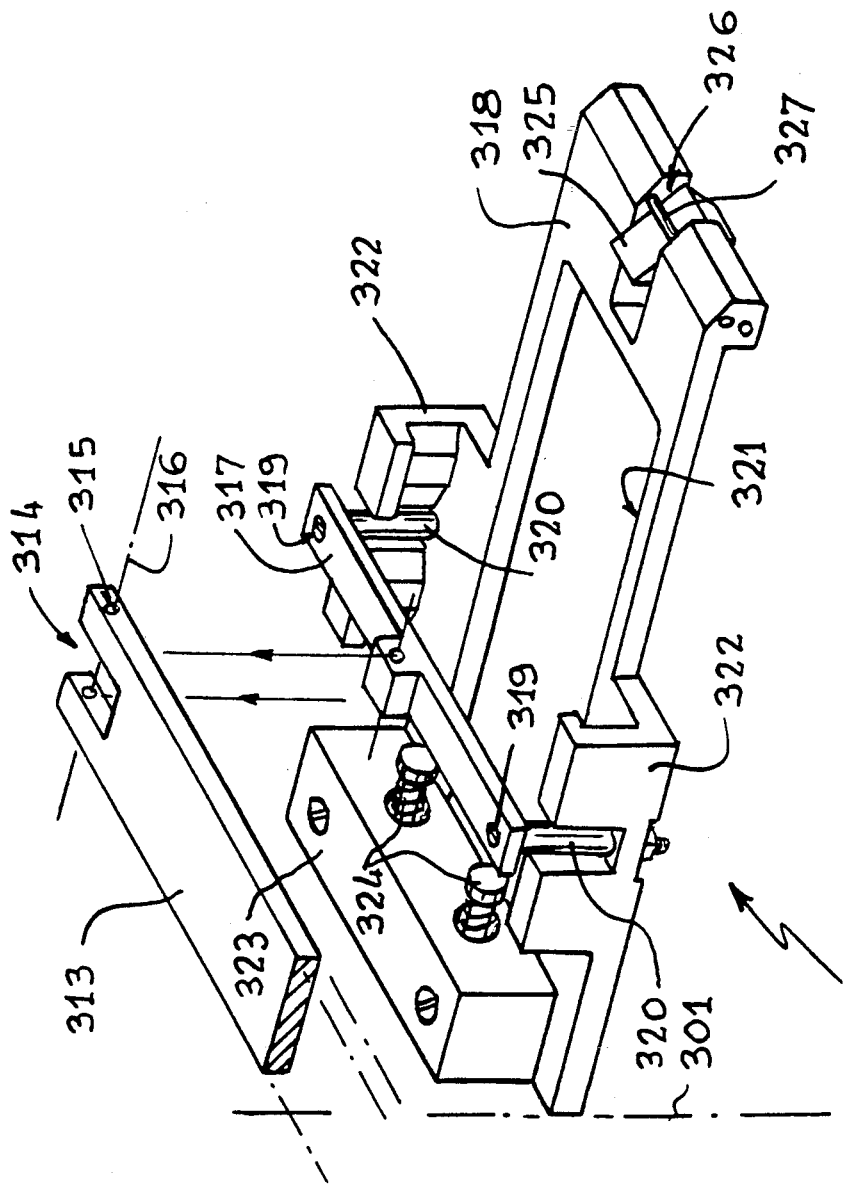
FIG. 3 is a view in perspective of one of the supports of the centrifuge.

The upper end of the shaft 301 supports a beam 313 of which the ends 314, in the form of fork joints (cf. FIG. 3), each provided with a bore 315 for the passage of a rotating pin 316 mounted on needle bearings.

Between the arms of each fork joint 314 is engaged a horizontal bar 317 adapted to pivot about the pin 316 and secured to a micro-board support 318 via screws 319 provided with spacers 320 so as to be offset in height with respect to the support 318.

Figure 4:
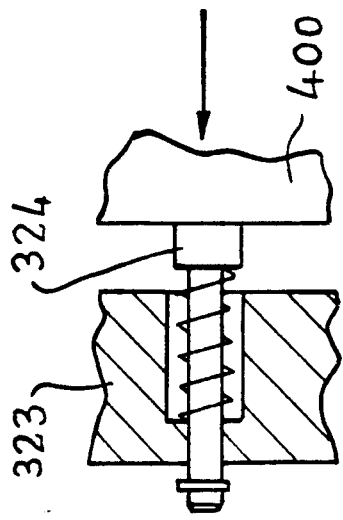
FIG. 4 is a view in detail of the means for blocking the micro-board in the support.

The micro-board support 318 is in the form of a T in which a recess 321 has been made. In the horizontal part of the T and on each of its lateral edges, grooved flanges are provided 322 formed on each side of the spacers 320. In the vertical part of the T, a block 323 is provided with springed stops 324 (FIG. 4) to which are opposed a pivoting lock 325 housed in a notch 326 provided with a stop 327 in order to limit rotation of the lock.

Figure 5:
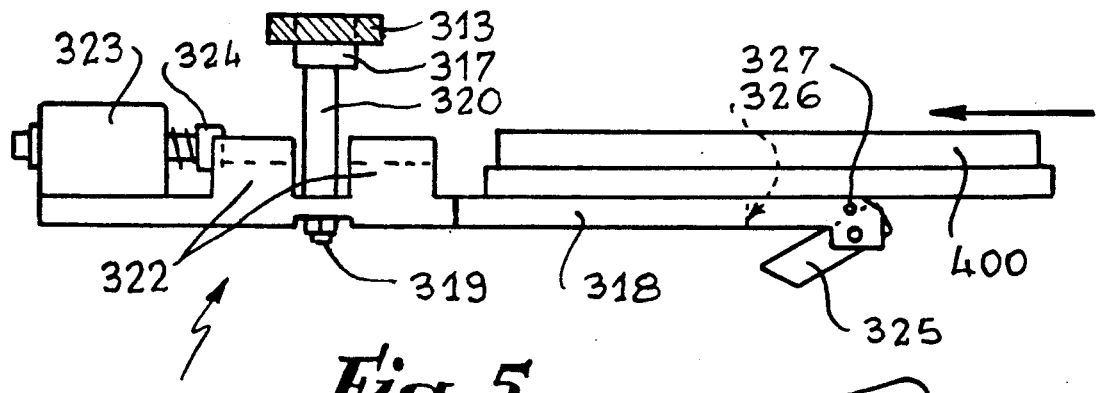
FIGS. 5 to 7 illustrate the positioning and locking of the micro-boards.
Figure 6:
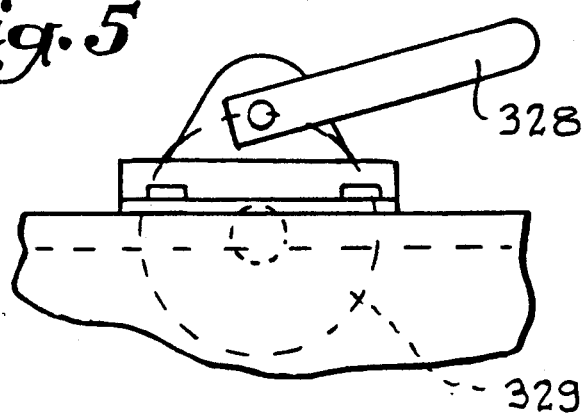
Figure 6:
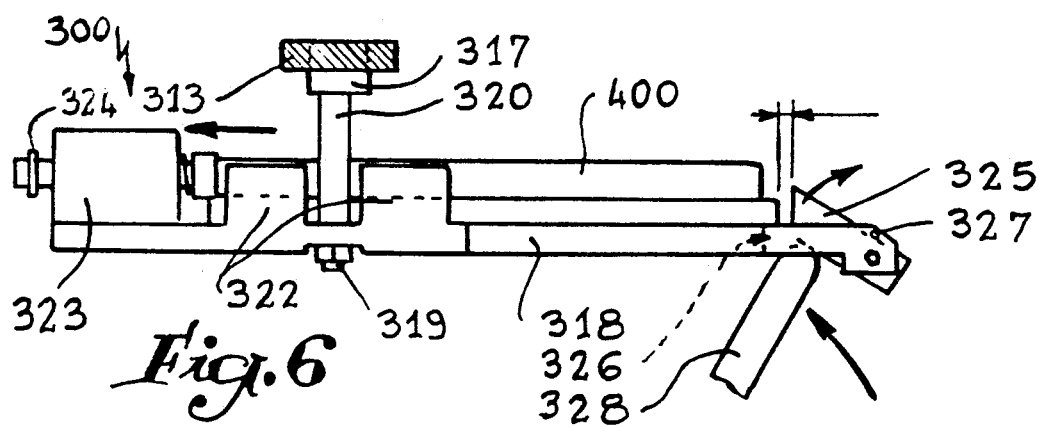
Figure 7:
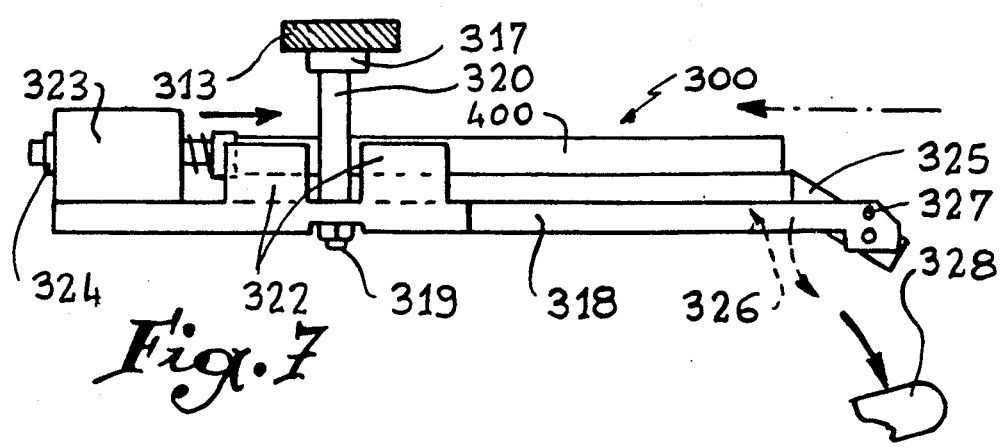

FIGS. 5 to 7 illustrate the positioning and locking of a micro-board 400 in a support 318 of the centrifuge 300 of the analyzer automat 100. The micro-board 400 is placed in position by hand, while locking is effected with the aid of the transfer clamp 500 and with a finger 328 controlled in rotation by a stepping motor 329 mounted in the table 200.

The functioning allowing the micro-board to be locked will be better explained hereinbelow.

FIG. 8 shows the transfer clamp 500 made of synthetic material having a recess 501 in its front part in the form of an upturned U, so that its opening is located on one of the wider edges of the clamp.

Each of the inner, opposite faces 502 and 503 of the recess 501 is provided with grooves 504 and 505 enabling the micro-board 400 to be guided axially and maintained by cooperating with the shoulders 401 provided on the periphery thereof.

It may be noted that the micro-board 400, known per se includes on its upper face 402, a series of cells 403 arranged in 8 rows and 12 columns and, on the other hand, shoulders 401 scored at 404, of which the function will be better explained hereinbelow.

The front face 506 of the clamp 500 includes two holes 507 and 508 opening in the groove 505 in the inner face 503 of the recess 501 in order to secure two thrust ball bearings 509 (FIG. 9) and 510 which cooperate with the scores 404 of the shoulder 401 of the micro-board 400 in order to retain it axially in the clamp 500.

A notch 511 is made in the face opposite the opening of the recess 501 so as to allow passage for the pivoting lock 325 of the micro-board support 318 during locking of the micro-board 400.

The clamp 500 is traversed in its rear part by two guide bars 512 and 513, which are at one of their ends with a mobile support 514 controlled in translation along the x-axis XX' by a belt 515 and a stepping motor 520 shown in FIG. 1. The clamp 500 slides along guide bars 512 and 513 by another belt 516 fixed on the clamp via a clip 517 and driven by another stepping motor 521 (FIG. 1).

Displacements of the clamp 500 along the x-axis XX' or the y-axis YY' may either be simultaneous or independent.

FIG. 10 shows the station 600 for sampling the products to be dispensed in the cells 403 of the micro-board 400. This sampling station is constituted by a vertical bracket 601 fixed on the table 200 and which includes at its upper end, a fixed guide 602 under which is provided a freely rotating pulley 603, and, at its lower end, another fixed guide 604 above which another pulley 605 is mounted on the driven shaft of a stepping motor 606 and is connected to pulley 603 via a drive belt 607.

Guides 602 and 604 have an opening aligned for the passage of a vertical guide shaft 608 of which the lower end cooperates with the driven shaft of a stepping motor 609 located beneath table 200. The motor 609 drives shaft 608 in rotation in either direction.

Between guides 602 and 604 are provided a support 610 secured with shaft 608 and a vertical shaft 611. A horizontal beam 612 is mounted for free rotation and translation on shafts 608 and 611.

The free end of the beam 612 includes a sampling probe 613 allowing dispensing of the products contained in the test-tubes 950 and a clip 614 fixed on the belt 607 driver beam 612 vertically along the shaft 608 and 611.

FIG. 11 shows the dispensing station 700 set up in an opening 201 in the transfer table 200. It is composed of a shaft 701 fixed in rotation by its lower end which is clamped in a plate 202 located under the table 200. The shaft 701 or rotating pin comprises, above the plate 201, a ring 702 provided in its inner part with a roller bearing device 703, while the outer part includes, in its middle, a crown 704 having holes 705. The crown 704 is sandwiched between a pulley 706 and a disc or rotor 707 made of plastic material and is secured by screws 708. The pulley 706 is driven in rotation via a belt 712 and another pulley 709 mounted on the driven shaft 710 of a stepping motor 711. The rotor 707 is centered on the ring 702 so as to be located in the opening 201 in table 200. The rotor 707 includes on its periphery a certain number of numbered notches 713 allowing the base of the test-tubes 950 to be retained. In addition, the rotor 707 is indexed in its rotation by a device (not shown) so as to present each test-tube 950 below the sampling probe 613.

The upper end of the shaft 701 supports a freely rotating arm 714 to the free end of which is mounted a container 715 for diluting the products to be dispensed and for washing the sampling probe 613.

The functioning and mode of using the analyzer automat 100 described above will be readily understood. An operator must proceed as follows:

He/she introduces, by hand, two micro-boards 400 in the supports 318 and between the grooved flanges 322 of the centrifuge 300. The test-tubes 950 are also placed in the notches 713 of the dispensing station 700.

Firstly, the tubes containing the reagents are placed in the notches numbered from 1 to N (being given that the number of reagents may vary depending on the type of analyses effected) and then the tubes filled with centrifuged blood of each of the patients to be analyzed.

An electronic control unit (not shown) is activated which will take over the analyzer automat 100 so that it carries out the following steps until the result of analysis is obtained:

Locking of the micro-boards 400 in the supports 318 by means of the transfer clamp 500 effected as follows (FIGS. 5 to 7):

clamp 500 lying slightly above the support 318 may engage the micro-board 400 in the grooves 504 and 505 of recess 501 in order to push it against spring-loaded stops 324 so that the finger 328 raises the pivoting lock 325 which is housed in the notch 511 of the clamp and against the end-of-stroke stop 327 of the support 318. Clamp 500 is then withdrawn, which, under the effect of the spring-loaded stops 324, provokes a lateral displacement of the micro-board 400 which comes into contact with the pivoting lock 325 in order to be blocked laterally and horizontally by the grooved flanges 322 which cooperate with the shoulders 401 of the micro-board. The finger 328 is withdrawn so as to allow the centrifuge to pivot through a half revolution in order to effect the same operation on the second micro-board;

this step of locking the micro-boards allows initiation of the work cycle and ensures safe operation of the device.

Return of the clamp into initial position O.

Indexation of the centrifuge 300 via the device 307 so that the micro-boards are in transfer position.

Unlocking and transfer of the micro-board with the aid of the clamp 500 under the sampling station 600 and dispensing station 700. The micro-board 400 is released (FIG. 7) when it is engaged in the grooves 504 and 505 of the clamp 500, so as to push the spring-loaded stop 324 so that the pivoting lock 325 pivots downwardly under its own weight.

Identification of the test-tubes 950 by means of a CCD camera 910 and a bar-code reader 920.

reading of the level of blood to determine the quantity to be sampled, and of the positioning of the bar-code label including the patient's references, by CCD camera 910;

if the test-tubes 950 are correctly positioned, they are displaced in front of the bar-code reader 920 in order to note the patient's references and the number of the notch 713 of the rotor 707 and to enter the data in the memory of the control unit;

if the test-tubes 950 are incorrectly introduced, the electronic unit emits a signal to the operator who must place them in the correct position.

Sampling of the centrifuged blood (red blood corpuscles/serum) from each of the patients by means of the probe 613 in order to dispense it in the cells 403 of the micro-board 400;

such dispensing is effected in accordance with the reactive configuration chosen, as it may be either in a line or in a column, i.e. each line or each column represents a patient;

the probe 613 is washed in the recipient 715 between two samplings (diluted red blood corpuscles, serum, red corpuscles+serum) and between two patients.

Sampling of the reagents by the probe 613 and dispensing in accordance with the configuration chosen;

washing of the probe 613 in the recipient 715 between the reagents dispensed.

Shaking of the micro-board 400 by the displacement of the clamp 500 along the x-axis XX' and y-axis YY' at a variable frequency.

Transfer of the micro-board on the centrifuge.

Locking of the micro-board.

Rotation of the centrifuge through a half-revolution and indexation if the micro-board has more than four patients to fill the second micro-board:

either with physiological solution if the number of patients is less than 8 to 12 depending on the configuration chosen so as to balance the unbalance of the centrifuge;

or with a fresh batch of blood and reagents if the number of patients is greater than 8 to 12 depending on the configuration.

Centrifugation of the micro-boards 400 for 2 mins. at 1400 rpm.

Re-indexation of the centrifuge for the filled first micro-board to be in transfer position.

Unlocking of the micro-board by means of clamp 500.

Shaking of the micro-board along the x-axis and y-axis of the clamp so as to place the possible agglutinates in suspension.

Displacement beneath the reading station 800 comprising a CCD camera 801 allowing interpretation of the results and display on the screen of the negative or positive spectrum of the blood group of each patient.

It will be observed that the manipulation of the micro-boards from the centrifuge to the different work stations may be effected by any other means.

It must, moreover, be understood that the foregoing description has been given only by way of example and that it in no way limits the domain of the invention which would not be exceeded by replacing the details of execution by any other equivalents.

What is claimed is:

1. An automat for analyzing blood groupings which includes a plurality of spaced work stations and wherein blood samples are carried in cells of micro-boards, the automat comprising, a centrifuge having a beam with opposite ends, a first motor for rotating said beam, a pair of support means for selectively retaining micro-boards therein, means for articulating said support means adjacent said opposite ends of said beam, each support means having a generally T-shaped profile and including a horizontal section oriented generally perpendicularly to a vertical section, said vertical section having end portions, a recess provided in said vertical section in which a micro-board may be selectively seated, said horizontal section including opposing flange members defining oppositely oriented grooves between which a micro-board may be selectively guided, a notch within one of said ends of said vertical section and a lock pivotally mounted within said notch and being opposed by a spring loaded stop mounted adjacent the opposite end of said vertical section, a transfer clamp for selectively moving the micro-boards from said centrifuge to said work stations, and a pair of stepping motors for moving said transfer clamp along first and second axes which are angularly oriented with respect to one another.

2. The automat for analyzing blood groupings of claim 1 including a stop means engageable by said pivoting lock when said pivoting lock is in a raised position with respect to said vertical section of said support means, a finger means mounted beneath said centrifuge and being selectively engageable with said lock to thereby urge said lock against said stop means, motor means for selectively activating said finger means, and said transfer clamp being engageable with the micro-boards mounted within said support means so as to urge said micro-boards against said spring loaded stops.

3. The automat for analyzing blood groupings of claim 2 wherein said transfer clamps include a recess in the configuration of a "U" having leg portions, said leg portions including oppositely oriented faces, a groove in each of said oppositely oriented faces in which said micro-board may be guided, and bearing means resiliently mounted within an opening provided in one of said leg portions for engaging said micro-board when said micro-board is within said grooves to thereby retain said micro-board within said recess of said transfer clamp.

4. The automat for analyzing blood groupings of claim 1 wherein said transfer clamps include a recess in the configuration of a "U" having leg portions, said leg portions including oppositely oriented faces, a groove in each of said oppositely oriented faces in which said micro-board may be guided, and bearing means resiliently mounted within an opening provided in one of said leg portions for engaging said micro-board when said micro-board is within said grooves to thereby retain said micro-board within said recess of said transfer clamp.

* * * * *